United States Patent
Atkinson et al.

(10) Patent No.: US 7,247,429 B2
(45) Date of Patent: Jul. 24, 2007

(54) BIOCHEMICAL AMPLIFICATION OF NUCLEIC ACIDS

(75) Inventors: George Robert Atkinson, Dorset (GB); Alysia Hallam, Dorset (GB)

(73) Assignee: Genetix Limited, Hampshire (GB)

( * ) Notice: Subject to any disclaimer, the term of this patent is extended or adjusted under 35 U.S.C. 154(b) by 111 days.

(21) Appl. No.: 10/212,732

(22) Filed: Aug. 7, 2002

(65) Prior Publication Data

US 2004/0029235 A1    Feb. 12, 2004

(51) Int. Cl.
  *C12Q 1/68* (2006.01)
  *C12P 19/34* (2006.01)
(52) U.S. Cl. .................. 435/6; 435/91.1; 435/91.2
(58) Field of Classification Search ............... 435/6, 435/91.1, 91.2
  See application file for complete search history.

(56) References Cited

U.S. PATENT DOCUMENTS

| | | | | |
|---|---|---|---|---|
| 5,104,792 | A * | 4/1992 | Silver et al. ................ | 435/6 |
| 5,618,664 | A * | 4/1997 | Kiessling ..................... | 435/2 |
| 6,312,893 | B1 * | 11/2001 | Van Ness et al. ............ | 435/6 |
| 6,350,580 | B1 * | 2/2002 | Sorge ........................... | 435/6 |
| 6,843,962 | B2 * | 1/2005 | Haslam et al. ............... | 422/65 |

FOREIGN PATENT DOCUMENTS

| EP | 0 913 465 A1 | 5/1991 |
|---|---|---|
| EP | 0 535 612 A1 | 4/1993 |
| WO | WO 01/97616 A1 | 12/2001 |

OTHER PUBLICATIONS

Willerslev et al., "Diversity of Holocene life forms in fossil glacier ice," PNAS, Jul. 1999, vol. 96, pp. 8017-8021.*
Fox et al., "Elminating PCR contamination: is UV irradiation the answer?" Journal of Virological Methods, 1991, vol. 33, pp. 375-382.*
Meldrum, "Automation for Genomics, Part One: Preparation for Sequencing," Genome Research, 2000, vol. 10, pp. 1081-1092.*
BioPick® product publication, Genomic Solutions, available on www.GenomicSolutions.com.*
U.S. Appl. No. 10/144,763, filed May 15, 2002, Ruddock.
U.S. Appl. No. 10/133,904, filed Apr. 29, 2002, Haslam et al.
Patent Abstracts of Japan, Mar. 27, 2001 & JP 11263314 (Hoya Schott KK) Sep. 17, 1999 (Abstract).

* cited by examiner

*Primary Examiner*—Young J. Kim
(74) *Attorney, Agent, or Firm*—Foley & Lardner LLP

(57) ABSTRACT

A method of cleaning a pin head or other implements between handling a plurality of samples of nucleic acid subject to an amplification process using a biochemical amplification product. The method comprises exposing the pin head or other implement to ultraviolet (UV) and preferably also infrared (IR) illumination between handling different samples in order to suppress cross-contamination by non-specific amplification. The biochemical amplification product may be obtained from a rolling circle amplification (RCA) procedure, such as that catalyzed by bacteriophage phi29, or a polymerase chain reaction (PCR) amplification product.

15 Claims, 1 Drawing Sheet

BIOCHEMICAL AMPLIFICATION OF NUCLEIC ACIDS

BACKGROUND OF THE INVENTION

Figure 1:
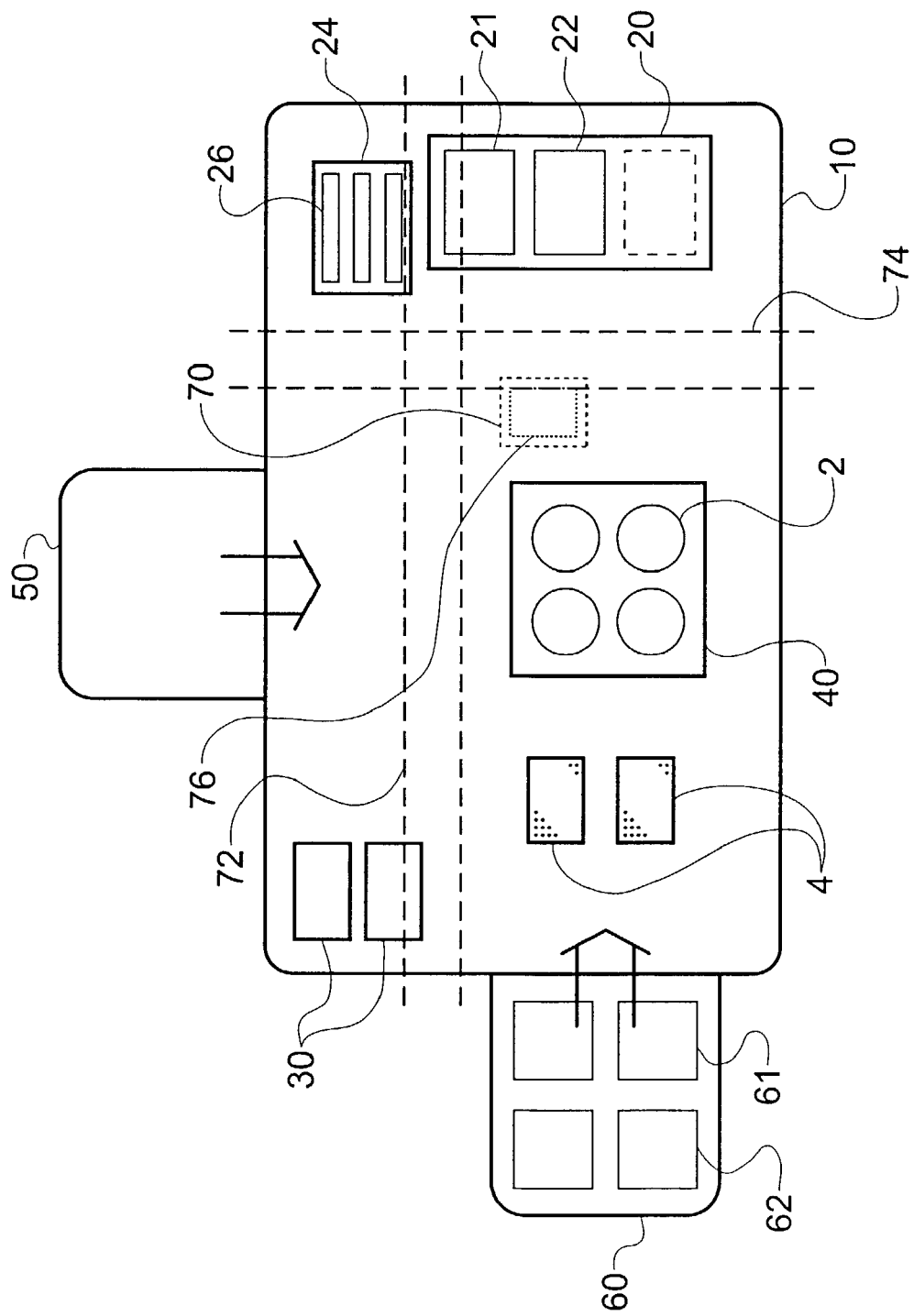

The invention relates to amplification of nucleic acids using biochemical amplification products, and in particular how to carry out such amplification in an automated fashion using robotic colony pickers and well plates.

As is well known, sequencing methods such as gel capillary electrophoresis require large numbers of copies of the genetic material of interest. It is therefore necessary to provide an efficient amplification process for replicating a small sample of the genetic material of interest.

Traditional amplification processes are based on inserting a sample of the nucleic acid of interest, e.g. a DNA or RNA fragment, into bacterial plasmids or artificial chromosomes, and then returning the recombinant material thus obtained into a bacterial or yeast host. Bacterium division or yeast division is then promoted by growing colonies of the bacteria or yeast in culture to provide the desired amplification, i.e. multiple copying. A typical culturing time is 24 hours. Following amplification, the samples are purified prior to sequencing.

More recently, biochemical amplification products have become available, for example the enzyme from bacteriophage phi29, marketed under the trade name "TempliPhi" by Amersham Biosciences. Biochemical amplification products include ones based on rolling circle amplification (RCA), such as bacteriophage phi29, and ones based on polymerase chain reaction (PCR), such as Taq polymerase or other thermostable DNA polymerase.

In principle, biochemical amplification offers several advantages over amplification in a bacterial or yeast host.

Firstly, the amplification process, being an essentially chemical rather than biological process, can be made quicker, since it is not dependent on culturing. For example, DNA sequences can be determined directly from bacterial colonies avoiding the necessity for growing colonies in culture.

Secondly, the amplified sample can be directly sequenced without the need for an intermediate purification step.

However, at least some biochemical amplification products are not compatible with colony picking robots because of contamination problems. Contamination is a specific problem with biochemical amplification products, because they are extremely sensitive to non-specific amplification. To understand the contamination problem when using colony picking robots, the basic operation of a colony picking robot is briefly described.

A colony picking robot uses a pin head comprising an array of pins each of which can be "fired" pneumatically, where firing is used to describe the pneumatically driven extension and retraction of each pin to and from a deployed position. The pins are arranged in an array matched to standard well plate dimensions. For example a 12×8 pin head is common with the pins laid out in a square grid matched to a 96-well well plate. The pin head is movable over the bed of the robot using high precision xyz-positioners. An individual colony is picked by moving the picking head over the colony of interest, which may be contained in a culture dish or tray clamped to the bed of the robot, so that an as-yet unused pin is over the colony. The pin is then fired down to touch the colony and thereby pick up sample from the colony. The pin is then retracted. The pin head is then moved to a well plate in which the sample is to be deposited. The pin carrying the sample is arranged over the well of the well plate chosen to receive that sample and the pin fired once again so that the pin head is immersed in solution contained in the target well (i.e. buffer), thereby releasing the sample into the well (i.e. inoculating).

Once all the pins have been used, and hence are "dirty", the pin head is moved to a wash station for cleaning. The wash station will have one or more baths. For example a wash station may have a single ethanol bath. Another example would be to have two baths, one containing ethanol and the other a mixture of bleach and distilled water. All pins of the pin head are fired into the cleaning liquid and washed. Washing may be assisted by mounting the bath on a shaker.

After washing and subsequent drying, the pins on the pin head are clean and available for further colony picking and inoculation.

With traditional amplification in a bacterial or yeast host, which is essentially a biological process, it is only necessary that any bacterium or yeast host on the pin heads is killed in the cleaning step performed at the wash station. Provided that the host is killed, it cannot divide, so amplification cannot occur. In the context of a picking robot, this means that, even if dead host material is left on a pin head after cleaning, contamination of a sample in another well by adding some of the dead host material from a previous picking event into it will not harm the process, since the contaminant material cannot be amplified. Amplification of a contaminant is referred to as non-specific amplification. In practice it has been found that when using colony picking robots non-specific amplification can be avoided with bacterial or yeast hosts without difficulty by thorough washing.

On the other hand, with biochemical amplification, which is essentially a chemical process, what is relevant is that the pin heads do not carry any chemically active residue from a previous sample after cleaning. Moving from a biological to a chemical process therefore imposes much more stringent requirement on the pin cleaning. In particular, it has been found that it is not feasible to carry out processes with the (bio)chemical amplification product bacteriophage phi29 in a colony picking robot with standard washing protocols, because of the cross-contamination and resultant non-specific amplification.

SUMMARY OF THE INVENTION

According to the invention there is provided a method of cleaning an implement between handling a plurality of samples of nucleic acid subject to an amplification process using a biochemical amplification product, wherein the method comprises exposing the implement to UV illumination between handling different ones of the samples in order to suppress cross-contamination by non-specific amplification.

By way of example, the avoidance of cross-contamination of nucleic acid samples is especially important when handling genomic DNA, in particular for whole genome amplification and subsequent application to SNP analysis, genotyping, forensic analysis or differential hybridization. The invention is not limited to DNA samples but may be applied to RNA and other types of nucleic acid material.

It is believed that UV illumination of the nucleic acid sample chemically modifies it by a photo-induced reaction. As is known, UV light affects nucleic acid samples by causing pyrimidine dimers and other photoproducts to form which prevent subsequent polymerase replication. Since the dimers and other photoproducts disrupt the normal replication, although residue may be left on the pins, it is inactivated since the amplification product cannot amplify a base pair section corrupted in this way. The novel use of UV exposure as part of the implement cleaning process when using biochemical amplification products thus exploits this known effect in a novel way to allow biochemical amplification products to be used in colony picking robots without non-specific amplification problems.

It is noted that a colony picking robot with UV illumination facility has been used in the prior art for killing yeast spores by heating. However, it is not believed that UV illumination has previously been used in conjunction with biochemical amplification products to induce photochemical reactions to inhibit subsequent replication and transcription as proposed by the present invention to prevent non-specific amplification.

Some embodiments of the invention use a rolling circle amplification (RCA) product. Other embodiments use a polymerase chain reaction (PCR) amplification product. The RCA product can be a bacteriophage enzyme. In particular, the method of the invention has been found to work well with bacteriophage phi29.

PCR can be used to screen genomic or cDNA libraries for presence of a particular gene; to identify ends of clones e.g. BACs to find overlapping clones; to find mutations e.g. by AFLP (amplified fragment length polymorphism), or by presence/absence of bands; in gene mapping; to amplify DNA for arraying on nylon membranes or glass microarrays; to produce PCR fragments for DNA sequencing.

RCA technology is designed for rapid amplification of DNA templates for direct use in sequencing, with no need for further purification. This in vitro amplification eliminates the need for overnight cell culture and conventional plasmid preparations.

It is envisaged that the invention will be applied to colony picking robots and other sample handling robots which include a head comprising a plurality of pins or tips. UV illumination will be applied to the head, which thus constitutes the above-named "implement".

The UV illumination may be conveniently provided by one or more halogen lamps. The halogen lamp or other light source may also serve to provide infrared (IR) illumination to further promote heating of the implement being cleaned.

The method can be improved by subjecting the implement, e.g. the pins of a pin head, to a gas flow to promote cooling during and/or after the UV illumination. The gas flow will typically be a flow of air or an inexpensive gas such as nitrogen.

The UV illumination can be used in conjunction with conventional washing of the implement. The washing may take place before or after the UV illumination. Conventional ethanol and/or bleach and water washes may be used.

The invention further provides use of a robot comprising a head with a plurality of pins, tips or the like, wherein the method comprises providing a plurality of samples of nucleic acid, each to be subject to an amplification process using a biochemical amplification product, and wherein the pins or tips are exposed to UV illumination between handling different ones of the samples in order to suppress cross-contamination by non-specific amplification.

The pins or tips may be solid or hollow.

The invention also provides a method of amplification of a plurality of samples of nucleic acid using a biochemical amplification product, comprising handling the samples with an implement; and exposing the implement to UV illumination between handling different ones of the samples in order to suppress cross-contamination by non-specific amplification.

DETAILED DESCRIPTION

For a better understanding of the invention and to show how the same may be carried into effect reference is now made by way of example to FIG. 1 of the accompanying drawing which shows schematically in plan view a robot for carrying out processes according to the invention.

The robot comprises a main bed 10. On the main bed 10 there is arranged a wash station 20 including space for three baths, two of which are fitted with baths in the illustration. A first bath 21 containing ethanol and a second bath 22 containing a mixture of bleach and distilled water are shown. The wash station 20 is used for cleaning the pins of a pin head between inoculations to avoid cross-contamination between samples. The main bed 10 also accommodates an illumination and drying bay 24 arranged alongside the wash station 20. The illumination and drying bay 24 takes the form of a unit that is recessed by approximately 10 cm (4 inches) below the plane of the main bed and which is fitted with a light source 26 to illuminate out of the recess. Three individual light bulbs 26 are illustrated in the figure, consistent with a current implementation of the invention which uses three halogen lamps. The recess of the illumination and drying bay 24 is connected to an air duct (not shown) which runs under the main bed of the apparatus and through which air is blown out of the recess in order to promote drying and cooling of the pin head held above the recess. Drying is needed following the wash step. Cooling is needed in view of the radiative absorption of energy by the pins from the light source, which leads to the pin temperatures being elevated to up to 200° C. As will be appreciated, it is important that the pins are cooled to ambient temperature before they are used for further picking and inoculation. The halogen lamps used in the current implementation of the invention are standard quartz 300W linear lamps of the R7 type, e.g. Osram Haloline 64701 or Philips Plusline. The illumination and drying bay 24 is used to illuminate and dry the pins of a pin head after washing in the wash station 20, in order to complete the pin cleaning process, as described in more detail further below.

The main bed 10 is also provided with a number of shakers 30, two being illustrated. These are shaped and dimensioned to receive standard size well plates (e.g. standard 384 well well plates) and have motor drives, which lie under the main bed, for rapidly rotating the well plates to induce vortexing in the wells. The main bed 10 also has a light table 40 built into it. The light table 40 comprises a diffuse glass plate mounted flush with the main bed 10 of the apparatus with a white light source arranged under the plane of the main bed 10 to illuminate the glass plate from below. If a biological sample container is arranged on the light table 40, the illumination allows a vision system based on a camera held above the main bed to identify the positions and sizes of colonies in the biological sample container for subsequent picking.

Attached to the upper side of the main bed 10 of the robot, as viewed in the illustration, is an automated biological sample container feeder 50. The container feeder 50 has a "hotel" type container store (not shown) with twenty-five shelves which can be driven up and down by a motor to align any one of the shelves with a conveyer that is used to deliver the containers from the container store (the "hotel") to the main bed of the apparatus. Each shelf can carry a single Q-Tray, a single Omnitray held in a Q-Tray shaped carrier, or four Petri dishes held in a Q-Tray shaped carrier. The conveyer is based on a pair of rails (not shown) which guide the containers onto the light table 40 through a delidding/ relidding mechanism (not shown) for removing and replacing the container lids as the containers are delivered to the main bed and returned to the container store respectively. By way of example, the illustration shows four Petri dishes 2 which have been delivered to the light table 40. For the sake of brevity, the mechanical design of the container feeder is not illustrated or described further. For further details of the container feeder, reference is made to co-pending U.S. patent application Ser. No. 10/133,904, the contents of which -are incorporated herein by reference.

Attached to the left end of the main bed 10, as viewed in the illustration, is an automated well plate feeder 60. The well plate feeder has one to three delivery lanes (two in this example) along which the well plates are supplied to and from the main bed of the apparatus through a delidding/relidding mechanism (not shown) for removing and replacing the well plate lids as the well plates pass through. By way of example, two well plates 4 are illustrated at the end of their delivery lanes. Each delivery lane is supplied from a feed port 61 to which is docked a cassette filled with well plates. Each feed port 61 has a supply mechanism that deposits well plates, one at a time, onto the delivery lane. Behind each of the feed ports 61 there is arranged a restack port 62 which has a pneumatically driven lifting mechanism for inserting well plates returned from the main bed of the apparatus into a further cassette. On their return, the well plates pass through the feed ports 61 before reaching the restack ports 62. For the sake of brevity, the mechanical design of the well plate feeder is not illustrated or described further. For further details of the well plate feeder, reference is made to co-pending U.S. patent application Ser. No. 10/133,904, the contents of which are incorporated herein by reference.

The robot has a manipulation head 70 which is movable over the main bed of the apparatus by x- y- and z-positioners 72, 74 and 76 respectively. The manipulation head 70 is carried by the z-positioner, which is in turn carried by the y-positioner, which is carried by the x-positioner. These items are shown schematically with dashed lines. Adjacent the manipulation head 70 the z-positioner 76 has attached thereto a camera for machine vision (not shown). The camera can be used for colony identification and for reading bar codes on the well plates and/or biological sample containers. Adjacent the manipulation head 70 the z-positioner 76 may also have attached thereto a well plate gripper (not shown) to allow well plates to be moved around the main bed of the apparatus. The manipulation head 70 is detachably mounted on the z-positioner 76 so that the head type can be changed. A pin head would be used for colony picking. A liquid handling head having an array of micropipette tips would be used for well plate liquid handling, such as transfer of liquid between well plates or filling of well plates with a buffer solution, a master mix etc. A gel coring head could also be fitted if desired. Head exchange is assumed to be manually performed in the illustration, but automated head exchange could be provided. For further details of head design and automated head exchange, reference is made to co-pending U.S. patent application Ser. No. 10/144,763, the contents of which are incorporated herein by reference.

The effect of the light source on the pin cleaning process is now discussed. With the halogen lamp implementation, illumination of a pin head held above the illumination and drying bay for a period of 4-30 seconds has been found to be sufficient to eliminate cross-contamination problems when used on its own, or more commonly in addition to a conventional ethanol wash. It is believed from initial trials that the beneficial action of the light source in the pin cleaning process is dependent on providing UV radiation. Assuming that this supposition is correct, it is important that whatever lamps are used do not have UV blocking envelopes or coatings. Moreover, it is believed to be important that the light source emits a component of infrared (IR) radiation to promote heating of the pins. The light source should therefore be chosen to be one without UV blocking or IR reflecting envelopes or coatings.

It is believed that UV illumination of the template (i.e. the sample of DNA or RNA to be amplified by the amplification procedure) chemically modifies it by a photo-induced reaction. As is known, UV light affects DNA by causing pyrimidine dimers and other photoproducts to form which prevent DNA polymerase replication through them. Pyrimidine dimers can form by covalent bonding between two pyrimidine bases (T or C) that are situated next to each other on a DNA or RNA strand. Since the dimers and other photoproducts disrupt the normal transcription and replication, although residue may be left on the pins, it is inactivated since the enzyme driving the RCA or PCR process cannot amplify a base pair section corrupted in this way. The novel use of UV exposure as part of the pin cleaning process when using RCA or PCR amplification products thus exploits this known effect to allow such amplification products to be used in colony picking robots without non-specific amplification.

Having described the robot used to carry out processes according to the invention, some example processes are now described using bacteriophage phi29 as an example of a rolling circle amplification (RCA) product and Taq polymerase as an example of a polymerase chain reaction (PCR) amplification product.

EXAMPLE 1

Bacteriophage Phi29 (TempliPhi™)

In the following, the main parts of the protocol are summarized in italics, with their implementation in terms of the detailed actions required written in normal script.

1. *A V-bottomed well plate with 384 wells, referred to in the following as the target well plate, is provided.* In the context of the robot, the target well plate is delivered to the main bed of the apparatus by the well plate feeder 60 by the lower delivery lane.

2. *The wells of the target plate are filled with 10 µl of sample buffer.* This is achieved by fitting a liquid handling head to the robot, wherein the liquid handling head has a 12×8 array of micropipette tips. Moving the liquid handling head over a buffer tank and lowering it. Filling the micropipette tips with buffer. Raising the liquid handling head and moving it to above the target well plate so that the 12×8 micropipette tips are above a first quadrant of the 384 well target well plate. Lowering the micropipette tips into the first quadrant. Discharging 10 µl of buffer into each of the wells of the first quadrant. Raising the liquid handling head, moving it across to a second quadrant and lowering it into the wells. Repeating this procedure until buffer has been discharged into all four quadrants so that all 384 wells contain 10 µl of buffer.

3. *Colonies are picked from agar in a source biological sample container in the form of a Petri dish (or other biological sample container).* The liquid handling head is exchanged for a pin head for colony picking that has a 12×8 array of pins arranged conformant to standard well plate spacing. A Petri dish 2 containing colonies grown in agar is delivered onto the light table 40 onto the main bed of the apparatus in a Q-Tray shaped carrier using the biological sample container feeder 50. The light table illumination is activated. The head 70 is moved over the Petri dish and its integrated vision system maps the colonies on the Petri dish according to location (x & y coordinates), size (diameter) or other user-selected criteria as appropriate. Colonies 1-96 identified by the vision system are picked onto individual pins of the pin head by pneumatic extension and retraction of each of the pins in turn in combination with appropriate movement of the xyz-positioning system. The pin head 70 is then moved over to the target well plate to position it above a first quadrant of the 384 wells. The picked colonies are then inoculated into the first quadrant of the target well plate by lowering the pins into the buffer solution with which the wells have previously been filled. The pin head is then raised and moved over to the wash station 20. The pins are washed in the bleach/distilled water bath, rinsed in a distilled water bath and then washed in an ethanol bath. Washing proceeds by pin immersion and shaking in the case that the wash station is mounted on its own shaker. The pin head 70 is then moved over to above the illumination and drying bay 24. The halogen lamps are switched on. The pins are exposed for a period of time in the halogen lamp, typically 4-30 seconds. The halogen lamps are switched off. The air blower is then switched on for a period of time sufficient to allow cooling of the pins to ambient temperature, typically 5-50 seconds with longer times being used for longer UV illumination periods. The pin head is now clean and ready to proceed further with the inoculation of the target well plate. Namely, Colonies 97-192 identified by the vision system are picked and the pin head moved over to above the second quadrant of the target well plate the wells of which are then inoculated. The pin head is then cleaned again with a combination of washing, UV illumination and blow drying/cooling. Colonies 193-288 are then picked and inoculated into the target well plate. The pin head cleaned again. Colonies 289-384 picked and inoculated, and the pin head cleaned again. If there are further colonies identified that need to be inoculated, the procedure is repeated with one or more further target well plates as necessary. For the sake of simplicity, the following description assumes that there is only a single target well plate.

4. The samples are vortexed vigorously. Using the well plate gripper on the head 70, the target well plate is arranged on one of the shakers 30 which is then switched on to vortex the samples. The V-shaped profile of the bottom of the wells promotes stable vortexing and prevents loss of sample through splashing.

5. A quantity of 5 µl of sample, i.e. one half of the sample, is transferred to a separate well plate for the TempliPhi RCA reaction, referred to as the second well plate in the following. (A strip tube could be used instead of the well plate.) To implement this with the robot, a well plate is first delivered to the main bed of the apparatus by the upper delivery lane of the well plate feeder 60. The sample is then transferred from the target well plate to the second well plate by refitting the liquid handling head to the robot and using it to syringe up 5 µl of liquid from each of the wells in the first quadrant of the target well plate and discharge them into the wells of a corresponding quadrant. The micropipette tips are then ejected down a waste chute (not shown) and a fresh set fitted on an anvil (not shown). The second quadrant is then processed and so forth until all four quadrants of the second well plate have been filled.

6. The samples in the second well plate are cooled to 4° C. for stable storage. Typically, this will be done by transferring the second well plate to an incubator, either manually or robotically. In the case of robotic transfer, the incubator can be arranged adjacent the main bed of the apparatus, and provided with an automated well plate feeder mechanism.

7.

8. The samples in the second well plate are denatured by heating the second well plate to 95° C. and maintaining it at that temperature for 3 minutes. This will be performed in an incubator or other suitable device, e.g. a heating block or thermocycler.

9. Following on from the manufacturer's protocol for TempliPhi, 5 µl of reaction buffer with 0.2 µl enzyme mix is added to each of the wells of the second well plate. To perform this step, the second well plate is returned to the main bed of the robot and a liquid handling head used.

10. The samples are mixed briefly by vortexing. This uses one of the shakers 30.

11. The samples in the second well plate are incubated for at least 12 hours at 30° C. To do this, the second well plate is transferred back to the incubator, either manually or robotically.

12. The samples in the second well plate are heated to 65° C. for 10 minutes & cooled to 4° C. in order to inactivate the enzyme. This thermal cycling is performed in the incubator.

13. 4 µl of the reaction volume from each well of the second well plate is put directly into a sequencing reaction. Whatever sequencing protocol that is desired can then be followed.

Variations can be envisioned e.g. picking directly into the TempliPhi reaction buffer.

It will be appreciated that the above protocol with appropriate variation of the thermal parameters will be applicable to other RCA products suitable for colony picking applications as and when they become available.

EXAMPLE 2

Taq Polymerase PCR

For the sake of brevity, this example only describes the main process steps. How these steps can be implemented in terms of robotic and manual actions will be understood from the previous example.

1. A number of 384 well PCR plates are filled with the PCR buffer or with complete master mix.

2. Using a 96 pin pin head, groups of 96 colonies are picked from a source container, such as a Q-Tray, using the robot.

3. The colonies on the picking pins are inoculated into one of the PCR well plates.

4. The picking pins are cleaned using essentially the same procedure as in Example 1, namely a wash in a number of baths, followed by UV illumination with halogen lamps and blow drying/cooling.

5. Steps 2-4 are repeated as often as necessary until inoculation is complete.

6. After inoculation the PCR plates are transferred to a PCR machine for thermal cycling as required for the amplification.

It will be appreciated that this protocol can be applied to PCR products other than Taq polymerase, such as other thermostable DNA polymerase.

EXAMPLE 3

Variation of Example 2

A variation on the procedure of Example 2 is to use a duplicate picking process whereby the colonies are inoculated not only into PCR well plates but also into a second well plate containing growth medium, e.g. Luria Bertani (LB) broth, in order to create a well plate array of cultures corresponding to the PCR reactions.

It will be appreciated that although the foregoing description has provided detailed description of examples of the invention in terms of specific sizes of well plates, numbers of pins etc, the invention is applicable to any kind of well plates or other liquid sample storage device including pipetting equipment. It will also be understood that the UV-assisted cleaning process of the invention is applicable to implements other than pins or other colony picking implements. For example it can be applied to the cleaning of gel coring heads. Although the invention has been described with reference to picked colonies, it will be appreciated that the nucleic acid material may come from any source, including phage or purified DNA preparations of any type, for example plasmid, genomic DNA, RNA, or PCR product.

What is claimed is:

1. A method of cleaning an implement between handling a plurality of samples or a plurality of batches of samples of nucleic acid subject to a nucleic acid biochemical amplification process, wherein
    the implement comprises a plurality of pins for picking nucleic acid samples, and wherein
    the method comprises exposing the pins to illumination with radiation having an ultraviolet (UV) component between handling different samples or batches of the samples, wherein the exposure to the illumination is for a period of between about 4 and 30 seconds and is sufficient to suppress cross-contamination by non-specific amplification.

2. The method of claim 1, wherein the biochemical amplification process comprises rolling circle amplification (RCA).

3. The method of claim 2, wherein the RCA uses a bacteriophage enzyme.

4. The method of claim 3, wherein the bacteriophage enzyme is phi29 polymerase.

5. The method of claim 1, wherein the biochemical amplification process comprises polymerase chain reaction (PCR) amplification.

6. The method of claim 5, wherein the PCR amplification uses thermostable DNA polymerase.

7. The method of claim 6, wherein the thermostable DNA polymerase is Taq polymerase.

8. The method of claim 1, wherein the illumination further includes an infrared (IR) component.

9. The method of claim 1, wherein the illumination is provided by at least one halogen lamp.

10. The method of claim 1, further comprising subjecting the implement to a gas flow to promote cooling during and/or after the illumination.

11. The method of claim 1, further comprising washing the implement.

12. The method of claim 11, wherein the implement is washed in at least one of ethanol and a bleach/water mix.

13. The method of claim 1, wherein exposure to the ultraviolet (UV) component of the illumination inactivates the nucleic acid.

14. The method of claim 1, wherein exposure to the ultraviolet (UV) component of the illumination causes formation of photoproducts which prevent replication of the nucleic acid.

15. A method of using an implement to handle a plurality of samples or a plurality of batches of samples of nucleic acid subject to a nucleic acid biochemical amplification process, wherein the implement comprises a plurality of pins for picking nucleic acid samples, and wherein the method comprises:
    (a) picking a first sample of nucleic acid with a pin of the implement, or a first batch of samples of nucleic acid with pins of the implement;
    (b) exposing the pins to illumination with radiation having an ultraviolet (UV) component for a period of between about 4 and 30 seconds; and
    (c) picking a second sample of nucleic acid with a pin of the implement, or a batch of samples of nucleic acid with pins of the implement.

* * * * *